United States Patent
Li et al.

(10) Patent No.: US 11,426,247 B2
(45) Date of Patent: *Aug. 30, 2022

(54) METHOD, SYSTEM FOR REGISTRATION OF BONE, AND TRACKABLE ELEMENT

(71) Applicant: Suzhou MicroPort Orthobot Co., Ltd., Jiangsu (CN)

(72) Inventors: Tao Li, Jiangsu (CN); Chao He, Jiangsu (CN); Hui Shao, Jiangsu (CN); Bin Song, Jiangsu (CN)

(73) Assignee: SUZHOU MICROPORT ORTHOBOT CO., LTD., Jiangsu (CN)

( * ) Notice: Subject to any disclaimer, the term of this patent is extended or adjusted under 35 U.S.C. 154(b) by 349 days.

This patent is subject to a terminal disclaimer.

(21) Appl. No.: 16/837,611

(22) Filed: Apr. 1, 2020

(65) Prior Publication Data

US 2021/0251711 A1    Aug. 19, 2021

(30) Foreign Application Priority Data

Feb. 19, 2020    (CN) .......................... 202010102880.9

(51) Int. Cl.
*A61B 34/00* (2016.01)
*A61B 34/10* (2016.01)
(Continued)

(52) U.S. Cl.
CPC .............. *A61B 34/74* (2016.02); *A61B 34/10* (2016.02); *A61B 34/20* (2016.02); *G06T 7/11* (2017.01);
(Continued)

(58) Field of Classification Search
CPC ........ A61B 2034/105; A61B 2034/107; A61B 2034/2046; A61B 2034/2055;
(Continued)

(56) References Cited

U.S. PATENT DOCUMENTS

2015/0328004 A1* 11/2015 Mafhouz ................... A61F 2/36
700/98

FOREIGN PATENT DOCUMENTS

CN     101160104 A    4/2008
CN     109496143 A    3/2019
(Continued)

*Primary Examiner* — Manuchehr Rahmjoo
(74) *Attorney, Agent, or Firm* — Muncy, Geissler, Olds & Lowe, P.C.

(57) ABSTRACT

The application provides a method, system for registration of a bone, and a trackable element, it is configured to obtain a mark point information which can be obtained from a certain operation performed by a distal end of a trackable element on a surface of the bone when a switch of the trackable element meets a setting condition corresponding to the operation; and to perform a virtual reconstruction of the surface of the bone according to the obtained mark point information and an image data of the bone which is obtained in advance. As a result, a precise registration of the patient's physical space coordinate system and image space coordinate system can be achieved, during which only one operator is enough for completing the registration. Therefore, operations with high accuracy and convenience are ensured, which can significantly improve the registration efficiency, and the operating experience of operators.

18 Claims, 5 Drawing Sheets

(51) Int. Cl.
*A61B 34/20* (2016.01)
*G06T 7/38* (2017.01)
*G06T 7/11* (2017.01)

(52) U.S. Cl.
CPC .......... *G06T 7/38* (2017.01); *A61B 2034/105* (2016.02); *A61B 2034/2046* (2016.02); *A61B 2562/02* (2013.01); *G06T 2207/30008* (2013.01)

(58) Field of Classification Search
CPC ...... A61B 2034/2068; A61B 2090/065; A61B 2090/3983; A61B 2562/02; A61B 34/10; A61B 34/20; A61B 34/74; G06T 2207/30008; G06T 7/11; G06T 7/33; G06T 7/38

See application file for complete search history.

(56) References Cited

FOREIGN PATENT DOCUMENTS

| | | |
|---|---|---|
| CN | 109692041 A | 4/2019 |
| CN | 110547873 A | 12/2019 |
| KR | 20200006331 A | 1/2020 |
| WO | WO-2010068212 A1 | 6/2010 |

\* cited by examiner

METHOD, SYSTEM FOR REGISTRATION OF BONE, AND TRACKABLE ELEMENT

CROSS-REFERENCE TO RELATED APPLICATION

This application claims the priority of Chinese patent application number 202010102880.9, filed on Feb. 19, 2020, the entire contents of which are incorporated herein by reference.

TECHNICAL FIELD

The application relates to the technical field of systems and methods for robot-assisted surgery and, more specifically, to a method, system, control device for registration of a bone, and to a trackable element.

BACKGROUND

In conventional orthopedic surgery, it is necessary for a surgeon to be familiar with the anatomy of a human body. To establish the anatomy only relying on a hand-eye system makes it to be really dependent on the experience of a doctor. In a computer-assisted orthopaedics surgery (CAOS), a computer is used for collecting original data of the patient and three-dimensional reconstruction, and provides three-dimensional models to guide the doctor, so that doctors can understand the progress of the surgery and direct the surgery by observing images on the computer, and even that the surgical planning can be done by the computer and the surgery can be done full- or semi-automatically after the doctor's confirmation. This kind of novel image-based navigation method makes it possible for doctors to use medical data to complete a surgery quickly, safely, and effectively, without relying on the doctor's own experience, which improves the safety of the surgery.

The existing navigation devices used in computer-assisted orthopaedic surgery usually require an operator to operate a trackable element to select points on the surface of the patient's tissue during preoperative registration, and it is also required to indicate to another operator for confirmation in the operating system when a point is selected, so as to complete the registration of the selected point. However, this kind of registration method requires at least two operators to cooperate for operation, which is not only time-consuming but also difficult to control the accuracy in determining the selection of points due to the instability of cooperative operations.

SUMMARY OF THE INVENTION

An objective of the present application is to provide a method, system, and control device for registration of a bone, and a trackable element, so as to solve the problems that existing navigation devices require at least two operators during preoperative registration, which is time-consuming and unreliable.

To solve the above technical problems, an aspect of the present application provides a registration method for a bone, comprising:

obtaining a mark point information through an operation performed by a distal end of a trackable element on a surface of the bone when a switch of the trackable element meets a setting condition corresponding to the operation;

performing a virtual reconstruction of the surface of the bone according to the obtained mark point information and an image data of the bone.

Optionally, the mark point information is obtained based on a surface profile data and a thickness data of a cartilage; or the mark point information is obtained based on a surface profile data of the bone;

wherein the surface profile data of the cartilage is obtained through an abutting operation performed by the distal end of the trackable element on a surface of the cartilage;

wherein the surface profile data of the bone is obtained through an abutting operation performed by the distal end of the trackable element on a surface of the bone;

wherein the thickness data of the cartilage is obtained by:

obtaining an information of a first position of the distal end of the trackable element when the switch of the trackable element meets a first setting condition and the distal end of the trackable element is at a selected point on the surface of the cartilage;

obtaining an information of a second position of the distal end of the trackable element when the distal end of the trackable element performs a puncture operation at the selected point and when the switch meets a second setting condition;

obtaining the thickness data of the cartilage based on a position variation between the first position and the second position.

Optionally, the mark point information is obtained based on a surface profile data and a thickness data of a cartilage;

wherein the surface profile data of the cartilage is obtained through an abutting operation performed by the distal end of the trackable element on a surface of the cartilage;

wherein the switch comprises a displacement contact switch with a damper, and the damper has a stiffness configured to allow a stroke of the damper to match a puncture resistance in a puncture operation performed by the distal end of the trackable element on the cartilage;

wherein the thickness data of the cartilage is obtained by:

obtaining a position information of the distal end of the trackable element when the distal end of the trackable element performs the puncture operation at a selected point and reaches a preset stroke of the damper;

obtaining the thickness data of the cartilage based on the stiffness of the damper and the position information.

Optionally, the mark point information is obtained based on the surface profile data of the cartilage and the thickness data of the cartilage;

wherein the thickness data of the cartilage comprises an average of a plurality of data obtained from puncture operations performed by the distal end of the trackable element on a plurality of selected points.

Optionally, the mark point information is obtained based on the surface profile data of the cartilage and the thickness data of the cartilage;

wherein the thickness data of the cartilage comprises an average of a plurality of data obtained from puncture operations performed by the distal end of the trackable element on a plurality of selected points.

Optionally, a step of performing a virtual reconstruction of the surface of the bone comprises:

registering a mark point set of the distal end of the trackable element with a positioning device and a surface point set resulting from segmenting the image data of the bone.

Optionally, registering a mark point set of the distal end of the trackable element with a positioning device and a surface point set resulting from segmenting the image data of the bone comprises:

transferring the mark point set $P_i$ to a coordinate system in which the surface point set $Q_i$ is located:

$$Q_i = R \cdot P_i + T$$

where R and T are rotation and translation matrices, and i is a natural number;

wherein the rotation and translation matrices R and T are selected to obtain a minimum of an objective function E:

$$E = \sum_{i=1}^{n} \|Q_i - (P_i \cdot R + T)\|^2 = \min.$$

An aspect of the present application provides a registration system for a bone, comprising: a trackable element, a positioning device and a control device;

wherein the trackable element is configured to perform an operation on a surface of the bone;

wherein the positioning device is communicatively connected to the trackable element and the control device, and the positioning device is configured to obtain a position information of the trackable element and send the position information to the control device;

wherein the trackable element comprises a switch communicatively connected to the control device, and the control device is triggered to obtain the position information of the trackable element when the switch meets a setting condition corresponding to the operation; and wherein the control device is configured to obtain a mark point information based on the position information, and perform a virtual reconstruction of the surface of the bone according to the mark point information in combination with an image data of the bone.

Optionally, a distal end of the trackable element is a pointed end; the distal end of the trackable element is configured to perform an abutting operation on a surface of a cartilage and to perform a puncture operation at a selected point on the surface of the cartilage; the control device is configured to:

obtain a surface profile data of the cartilage according to the abutting operation performed by the distal end of the trackable element against the surface of the cartilage, to obtain a thickness data of the cartilage according to the puncture operation performed by the distal end of the trackable element on the surface of the cartilage, and to obtain the mark point information based on the surface profile data and thickness data of the cartilage; or a distal end of the trackable element is configured to perform an abutting operation on the surface of the bone; the control device is configured to obtain a surface profile data of the bone according to the abutting operation performed by the distal end of the trackable element against the surface of the bone, and to obtain the mark point information based on the surface profile data of the bone.

Optionally, the switch is configured to trigger the control device to record an information of first position of the trackable element when the trackable element performs the puncture operation at the selected point on the surface of the cartilage and when a first setting condition is met, and to trigger the control device to record an information of second position of the trackable element when a second setting condition is met during the puncture operation; and the control device is configured to obtain the thickness data of the cartilage according to a position variation between the first position and the second position.

Optionally, the switch comprises a manual switch or a force sensor configured to sense a force received by the distal end of the trackable element;

the first setting condition comprises:
the manual switch is pressed; or
the force sensed by the force sensor is greater than a first preset value;

the second setting condition comprises:
the manual switch is pressed again;
the force sensed by the force sensor is greater than a second preset value, wherein the second preset value is greater than the first preset value; or
the position information of the distal end of the trackable element remains unchanged during an increase of the force sensed by the force sensor.

Optionally, the distal end of the trackable element is a pointed end, and the distal end of the trackable element is configured to perform a puncture operation at the selected point on the surface of the cartilage;

wherein the switch comprises a displacement contact switch comprising a damper, and the damper has a stiffness configured to allow a stroke of the damper to match a puncture resistance in a puncture operation performed by the distal end of the trackable element through the cartilage; the displacement contact switch is configured to trigger the control device to record the position information of the trackable element when a preset stroke of the damper is reached; the control device is configured to obtain the thickness data of the cartilage based on the position information and the stiffness of the damper.

Optionally, the switch is configured to trigger the control device to record the position information of the distal end of the trackable element when a third setting condition is met; the control device is configured to obtain the surface profile data of the cartilage or the surface profile data of the bone according to the position information.

Optionally, registration system further comprises a display device communicatively connected to the control device, wherein the display device is configured to display the position information of the trackable element, selected points on the surface of the bone, results of the virtual reconstruction, or a moving trajectory of the trackable element.

Optionally, the positioning device comprises an optical locator, and the trackable element comprises a plurality of optical targets;

wherein the optical locator is configured to position the optical targets with infrared rays.

An aspect of the present application provides a trackable element, comprising: a switch and a plurality of targets, wherein the targets are tracked by a positioning device; and the switch is configured to trigger a control device to obtain a position information of a distal end of the trackable element when a setting condition is met.

Optionally, the distal end of the trackable element is a pointed end, and the distal end of the trackable element is configured to perform a puncture operation at a selected point on a surface of a cartilage;

wherein the switch is configured to trigger the control device to obtain an information of first position of the trackable element when a first setting condition is met, and to trigger the control device to obtain an information of second position of the trackable element when a second setting condition is met during the puncture operation.

Optionally, the switch comprises a manual switch or a force sensor configured to sense a force received by the distal end of the trackable element;

the first setting condition comprises:
the manual switch is pressed; or
the reactive force sensed by the force sensor is greater than a first preset value;
the second setting condition comprises:
the manual switch is pressed again;
the force sensed by the force sensor is greater than a second preset value, wherein the second preset value is greater than the first preset value; or
the position information of the distal end of the trackable element remains unchanged during an increase of the reactive force sensed by the force sensor.

Optionally, the distal end of the trackable element is a pointed end, and the distal end of the trackable element is configured to perform a puncture operation at a selected point on a surface of a cartilage;

wherein the switch comprises a displacement contact switch comprising a damper, and the damper has a stiffness configured to allow a stroke of the damper to match a puncture resistance in a puncture operation performed by the distal end of the trackable element through the cartilage; the displacement contact switch is configured to trigger the control device to obtain the position information of the trackable element when a preset stroke of the damper is reached.

Optionally, the distal end of the trackable element is configured to perform an abutting operation on a surface of a cartilage or a surface of a bone, and the switch is configured to trigger the control device to record the position information of the distal end of the trackable element when a third setting condition is met.

In summary, in the method, system, control device for registration of a bone, and the trackable element provided by the present application, it is configured to obtain a mark point information which can be obtained from a certain operation performed by a distal end of a trackable element on a surface of the bone when a switch of the trackable element meets a setting condition corresponding to the operation; and to perform a virtual reconstruction of the surface of the bone according to the obtained mark point information and an image data of the bone which is obtained in advance. As a result, the virtual reconstruction of the surface of the bone can be achieved based on the certain operation which is corresponding to the control of the switch of the trackable element and is performed by a distal end of a trackable element on a surface of the bone, so that a precise registration of the patient's physical space coordinate system and image space coordinate system can be achieved, during which only one operator is enough for completing the registration. Therefore, operations with high accuracy and convenience are ensured, which can significantly improve the registration efficiency, and the operating experience of operators.

BRIEF DESCRIPTION OF THE DRAWINGS

Those of ordinary skill in the art will understand that the accompanying drawings are provided for better understanding of the present application, and do not limit the scope of the present application in any way.

Figure 1:
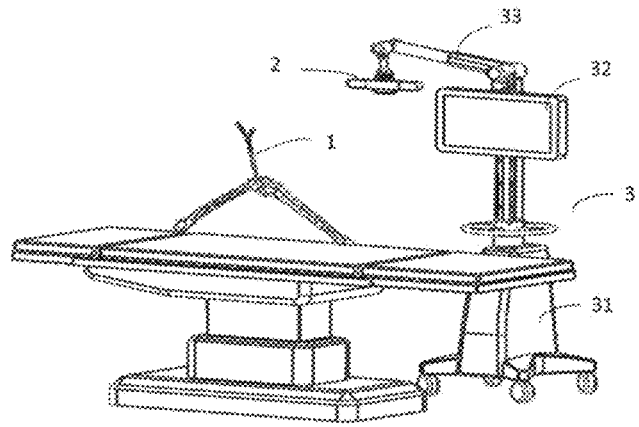
FIG. 1 is a schematic diagram of a system for registration of a bone according to an embodiment of the present application.

In the drawings:
1—trackable element; 2—positioning device; 3—navigation cart; 31—video cart; 32—display device; 33—link device; 34—target ball; 35—manual switch; 36—force sensor; 37—displacement contact switch; 41—virtual reconstruction area; 50—control device; 51—processor; 52—memory; 53—communication interface.

DETAILED DESCRIPTION

In order to make the objectives, advantages and features of the present application clearer, the present application will be further described in detail below with reference to the accompanying drawings and specific embodiments. It should be noted that the drawings are in a very simplified form and are not drawn to scale, and are only used to facilitate the description of the embodiments of the present application. In addition, the structures shown in the drawings may be a part of the actual structure. In particular, the drawings may show different parts in detail with different proportions.

As used in the present application, the singular form "a", "an", "One" as well as "the" may refer to a plurality of objects, the term "or" is usually understood as "and/or", the term "multiple" is usually understood as at least one, the term "at least two" usually includes "two or more". In addition, the terms "first", "second", and "third" are used for descriptive purposes only and cannot be understood as indicating or implying relative importance or implicitly indicating the number of the technical features. Therefore, the features defined by "first", "second", and "third" may explicitly or implicitly include one or at least two of the features. The term "proximal end" is usually the end close to the operator, the term "distal end" is usually the end close to the patient near the lesion, and "one end" and "the other end" and "proximal end" and "distal end" usually refer to two corresponding parts, which include not only the endpoints, unless the content clearly indicates otherwise.

The core idea of the present application is to provide a method, system, and control device for registration of a bone, and a trackable element, so as to solve the problems that existing navigation devices require at least two operators during preoperative registration of the bone, which is time-consuming and unreliable. The following description is made with reference to the drawings.

Figure 2:
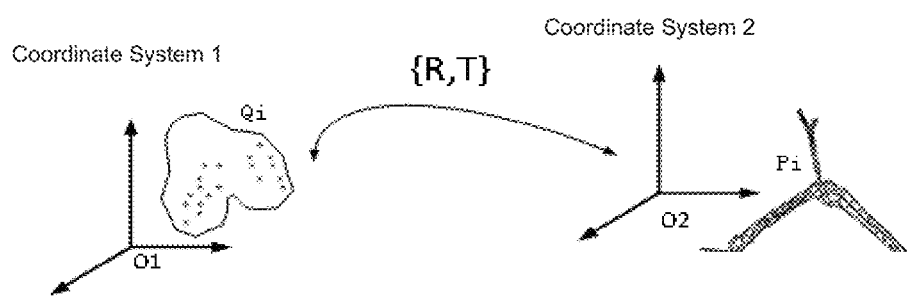
FIG. 2 is a schematic diagram of registration according to an embodiment of the present application.
Figure 3:
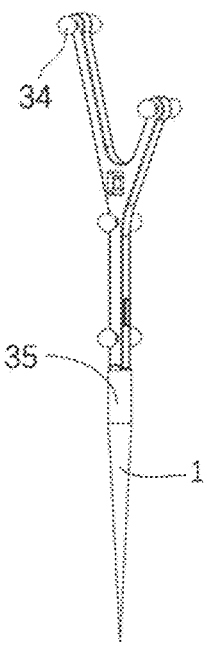
FIG. 3 is a schematic diagram of a trackable element according to a first example of an embodiment of the present application.
Figure 4:
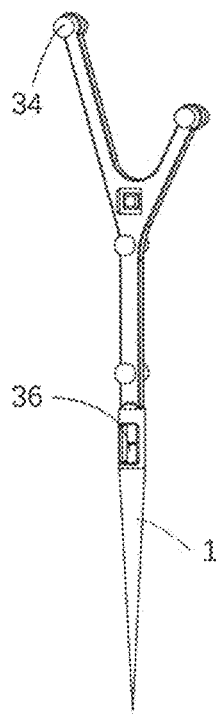
FIG. 4 is a schematic diagram of a trackable element according to a second example of an embodiment of the present application.
Figure 5:
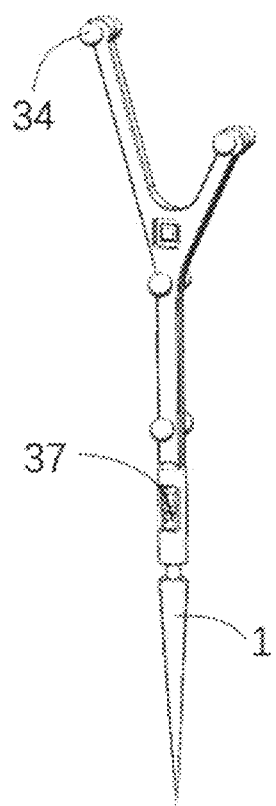
FIG. 5 is a schematic diagram of a trackable element according to a third example of an embodiment of the present application.
Figure 6:
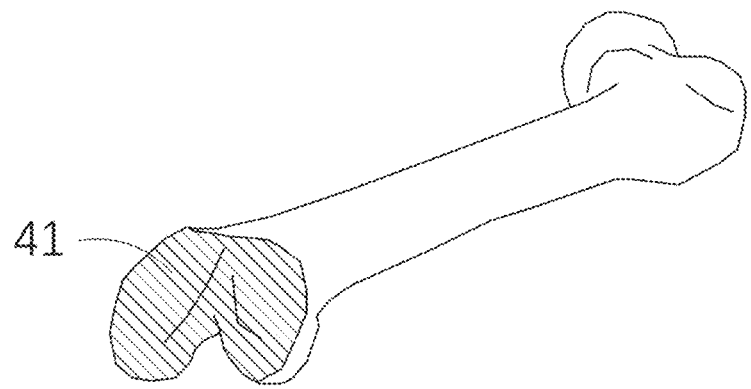
FIG. 6 is a schematic diagram of a virtual reconstruction of a surface of a bone according to an embodiment of the present application.
Figure 7:
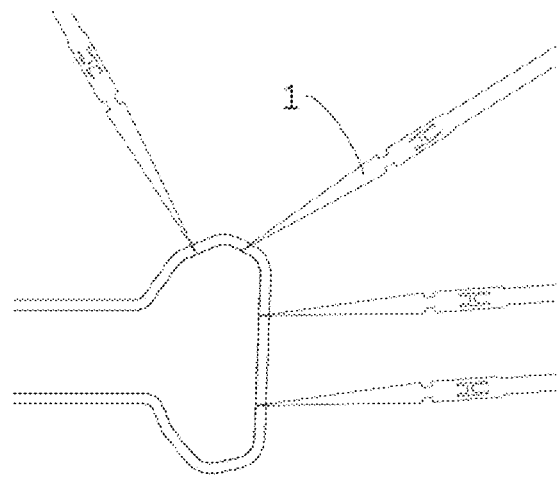
FIG. 7 is a schematic diagram of a puncture operation according to an embodiment of the present application.
Figure 8:
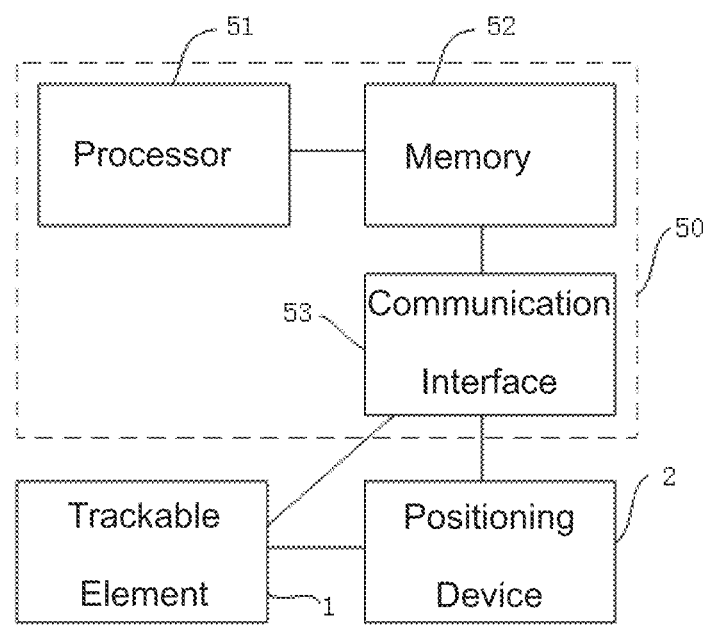
FIG. 8 is a schematic diagram of a control device for registration of a bone according to an embodiment of the present application.
Figure 9:
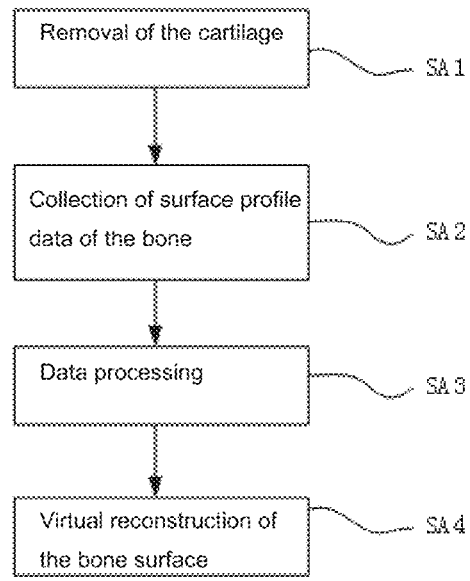
FIG. 9 is a flowchart of a method for registration of a bone with removal of a cartilage according to an embodiment of the present application.
Figure 10:
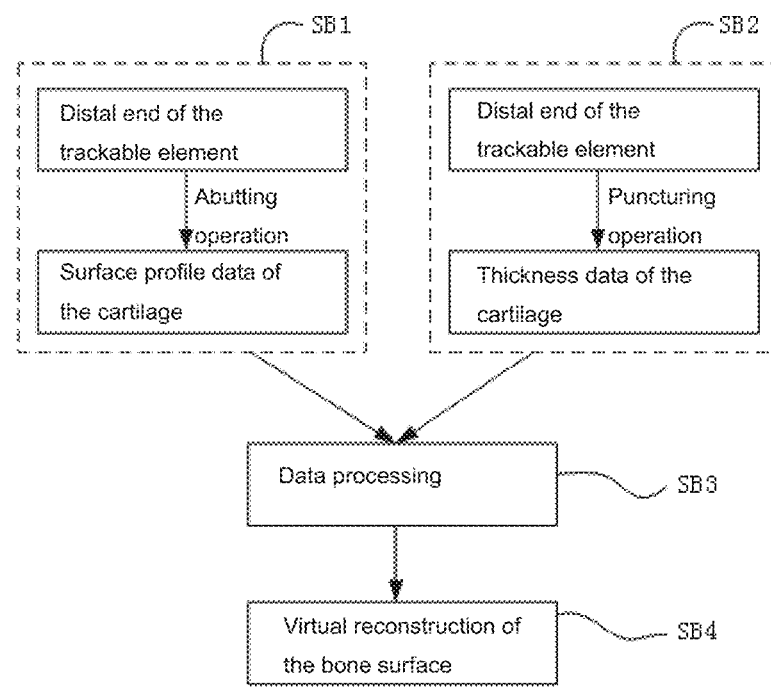
FIG. 10 is a flowchart of a method for registration of a bone without removal of a cartilage according to an embodiment of the present application.

Please refer to FIGS. 1 to 10, FIG. 1 is a schematic diagram of a system for registration of a bone according to an embodiment of the present application, FIG. 2 is a schematic diagram of registration according to an embodiment of the present application, FIG. 3 is a schematic diagram of a trackable element according to a first example of an embodiment of the present application, FIG. 4 is a schematic diagram of a trackable element according to a second example of an embodiment of the present application, FIG. 5 is a schematic diagram of a trackable element according to a third example of an embodiment of the present application, FIG. 6 is a schematic diagram of a virtual reconstruction of a surface of a bone according to an embodiment of the present application, FIG. 7 is a schematic diagram of a puncture operation according to an embodiment of the present application, FIG. 8 is a schematic diagram of a control device for registration of a bone according to an embodiment of the present application, FIG. 9 is a flowchart of a method for registration of a bone with removal of a cartilage according to an embodiment of the present application, FIG. 10 is a flowchart of a method for registration of a bone without removal of a cartilage according to an embodiment of the present application.

An embodiment 1 of the present application provides a system for registration of a bone. As shown in FIG. 1, the system includes a trackable element 1, a positioning device 2, and a control device. The positioning device 2 is communicatively connected to the trackable element 1 and the control device, and the positioning device 2 is configured to obtain a position information of the trackable element 1 and to send the position information to the control device.

As shown in FIG. 8, the control device 50 may have various functions described in this application, such as calculation and control. In some embodiments, the control device 50 is a computer, and the computer is preferably disposed on a navigation cart 3, but the present application is not limited thereto. In some other embodiments, the control device 50 is provided in a separate device or in a remote device. In still other embodiments, a part of the control device is arranged in the navigation cart 3, and the rest parts are set in one or more other separate devices. In a further embodiment, the control device 50 is selectively disposed at any position of the system. The control device 50 includes a processing circuit including a processor 51 and a memory 52. The processor 51 may be selected from a general-purpose processor, an application-specific integrated circuit (ASIC), one or more field-programmable gate arrays (FPGAs), a processing component, or other suitable electronic processing components; the memory 52 is one or various devices (such as RAM, ROM, flash memory, hard disk memory, etc.) for storing data and/or computer programs that are used to complete or assist various functions/processes described in this application; the memory 52 may be or include volatile memory or non-volatile memory; further, the memory 52 may include a database component, an object code component, a script component, or any other type of information structure for supporting the various functions described in this application. In an exemplary embodiment, the memory 52 is communicatively connected to the processor 51 and includes computer code for performing one or more functions/processes described in this application; the memory 52 includes at least one module, each module stores data and/or computer code related to a specific type of function in order to implement the function corresponding to each module.

The control device 50 further includes a communication interface 53 communicatively connected to the positioning device 2 and the trackable element 1. The communication interface 53 includes a wired or wireless interface, such as a socket, antenna, transmitter, receiver, transceivers, wire connectors, etc., which are not limited in this application. Such wired or wireless interface is connected to an external source directly or through a network, such as Internet, LAN, WAN or WLAN, in order for data transmission. In some embodiments, the communication interface 53 includes an Ethernet card and port for sending and receiving data via an Ethernet-based communication link or network; in other embodiments, the communication interface 53 includes a Wi-Fi transceiver for communication via wireless communication network. Before registration of a bone, preoperative image data in the form of two-dimensional images, three-dimensional models, etc. are transmitted to the control device 50 via the communication interface 53 and stored in the memory 52 for use in registration/preoperative planning. The preoperative image data may be scan data obtained by scanning the patient with any known imaging equipment, such as CT, MRI, ultrasound, and the like. The medical image segmentation device or the control device is used to segment the scan data to obtain a three-dimensional representation of anatomy of a target part of the patient. Specifically, the communication interface 53 is configured to obtain marker point information which is obtained through corresponding operations performed by the distal end of the trackable element 1 on a surface of a bone.

Preferably, the navigation cart 3 further includes a video cart 31 and a display device 32. The display device 32 and the control device are communicatively connected together through the communication interface 53, and the display device 32 is configured to display the position information of the trackable element 1, the selected points of the bone surface, the result of the virtual reconstruction of the bone surface, or the moving trajectory of the trackable element 1. The positioning device 2 is also preferably disposed on the navigation cart 3. In the exemplary solution shown in FIG. 1, the positioning device 2 is an optical position finder. The optical position finder is arranged on the upper part of the video cart 31 through a link device 33 so that the height and angle of the optical position finder can be adjusted relative to the video cart 31 so as to adapt to the position of the patient. In this case, the trackable element 1 can be observed without any obstruction. In some embodiments, the optical position finder is an optical positioning device provided with a plurality of infrared emitters. Correspondingly, a plurality of optical targets, such as target balls 34, are provided on the trackable element 1, and at least some of the target balls 34 can be observed and tracked by an optical position finder at a same time so that the target balls 34 can be tracked and positioned through infrared rays. Because of the target balls 34, the trackable element 1 can be paired with the optical position finder. The optical position finder is used to determine the position information of the distal end of the trackable element 1 in the physical coordinate system of the patient according to the position information of the target balls 34. The positioning device 2 is, but not limited to, an optical position finder, and the tracking element 1 is provided with, but not limited to, optical targets. Those skilled in the art can also make similar replacements according to the existing technology, such as magnetic navigation devices and magnetic targets.

The control device is preferably arranged in the video cart 31, but as described above, the specific position or arrangement of the control device is not limited in the present application. In an embodiment, the control device segments and extracts from pre-obtained bone image data, such as bone image data collected before surgery or preoperative image data (such as CT images), based on the physiological and shape characteristics of human tissues, to select points. The operator holds the trackable element 1 in hand to collect the corresponding mark points from the patient according to the above-mentioned selected points. Furthermore, the optical position finder 2 obtains position information of each marked point relative to the optical position finder 2. As shown in FIG. 2, the control device uses a point cloud registration algorithm to register the CT image collected before the operation with the marker points measured by the optical position finder, and extracts selected points on the CT image that are finely registered with the marker points. Through the fine registration of a certain number of marked points, the final transformation matrix is obtained, and the precise registration of the patient's physical space coordinate system and image space coordinate system is achieved. The display device 32 is disposed on the video cart 31, and the CT images collected before the surgery and the selected points can be superimposed and displayed on the display device 32. The display device 32 is a touch screen display, or is controlled by an input device such as a keyboard/mouse.

FIG. 3 shows the trackable element 1 according to the first example of this embodiment. The trackable element 1 is Y-shaped, that is, it includes a main body and two branches extending from the main body. The main body is roughly pen-shaped and the two branches have different lengths. In some embodiments, the lengths of the two branches are the same. The application does not specifically limit the length and positional relationship of the branches, as long as the target balls on the branches can communicate with the optical position finder. There are eight target balls 34 which are distributed on both sides of the trackable element 1 and are arranged symmetrically. On one side, two target balls 34 are located at the ends of one of the branches, one target ball 34 is located at the junction of the branches and the main body, and one target ball 34 is located in the middle of the main body. In the present application, the shape of the trackable element, the number of the target balls 34, and the arrangement thereof are not specifically limited. The shape of the trackable element, the number of target balls 34, and the arrangement thereof can be modified by those skilled in the art according to actual needs. According to the number of target balls 34 and arrangement thereof, those skilled in the art may use corresponding algorithms to determine the position information of the distal end of the trackable element in the patient's physical coordinate system.

The trackable element 1 further includes a switch communicatively connected to the control device, and the switch is configured to trigger the control device to obtain and record the position information of the trackable element 1 when a certain setting condition is met. In practice, the position information represents the mark point determined by the operator on the bone surface. When the switch meets a setting condition, the control device is triggered to be notified about the mark point determined by the operator. For example, the switch can be a manual switch 35 (such as a button switch), and in some embodiments, the setting conditions include pressing the manual switch 35 to activate the switch correspondingly to a preset rule (such as long press, short press or double-click, etc.). The manual switch 35 is selectively arranged at any position on the trackable element 1. In some embodiments, the manual switch 35 is arranged at a position that is easily touched by an operator when the trackable element 1 is held by the operator in hand. The manual switch 35 makes it convenient for the operator to perform real-time operations, including but not limited to the determination and deletion of mark points, without the assistance of other operators, which improves work efficiency and operating experience. In some other embodiments, the trackable element 1 is wirelessly connected to the communication interface of the control device via the manual switch 35. For example, the manual switch 35 is connected to the control device via Bluetooth. The registration result of the control device may be displayed on the display device 32. The operator can operate the manual switch 35 according to a prompt from the display device 32. The control device receives the mark signal of the manual switch 35, and controls the display device to display the mark point determination information (for example, displaying a green selected point) or the mark point redetermination or deletion information (for example, displaying a red selected point) to an operator, so that the determination or deletion of the mark point can be achieved. As a result, only one operator is enough for completing the registration work.

Furthermore, the present application does not limit the operation mode of the manual switch 35, as long as different functions can be realized through different input modes. In other words, the operator can operate the manual switch 35 in different ways to achieve different functions. For example, selection and deletion of the mark points can be achieved by pressing the manual switch 35 one time, multiple times, or long pressing the manual switch 35. For another example, a plurality of buttons corresponding to respective functions (such as OK and CANCEL buttons, etc.) are provided. In an exemplary example, when the operator presses the manual switch 35 twice, the confirmation of the mark point can be done; when the operator long presses the manual switch 35, the control device prompts the operator to delete the marked point, and when the operator presses the manual switch 35 again, the mark point is deleted, and when the operator long presses the manual switch 35 again, the deletion of the mark point is cancelled and then a mode for selecting mark points is reentered.

To solve the technical problem of the present application, this embodiment further provides a method for registration of a bone, which includes:

obtaining a mark point information which can be obtained from a certain operation performed by a distal end of a trackable element on a surface of the bone when a switch of the trackable element 1 meets a setting condition corresponding to the operation; and performing a virtual reconstruction of the surface of the bone according to the obtained mark point information and an image data of the bone which is obtained in advance. As a result, the virtual reconstruction of the surface of the bone can be achieved based on the certain operation which is corresponding to the control of the switch of the trackable element 1 and is performed by a distal end of a trackable element 1 on a surface of the bone, so that a precise registration of the patient's physical space coordinate system and image space coordinate system can be achieved, during which only one operator is enough for completing the registration. Therefore, operations with high accuracy and convenience are ensured, which can significantly improve the registration efficiency, and the operating experience of operators.

Further, a surface profile data of the bone can be obtained through an abutting operation performed by the distal end of the trackable element on a surface of the bone. In practice, a cartilage or soft tissue covers the surface of the bone. If the cartilage is removed and the distal end of the trackable element 1 is pressed against the surface of the bone, the surface profile data of the bone can be obtained. The control device obtains the mark point information based on the surface profile data of the bone. The control device thus performs a virtual reconstruction of the bone surface based on the mark point information and the bone image data obtained in advance. As shown in FIG. 9, the removal of the cartilage includes the following steps: Step SA1 removal of the cartilage; Step SA2: collection of surface profile data of the bone; Step SA3: data processing (performed by the control device, for example); Step SA4: virtual reconstruction of the bone surface (performed by the control device, for example).

In some embodiments, the cartilage may be removed from the surface of the bone by a milling cutter so as to expose the surface of the bone; then the distal end of the trackable element 1 abuts the surface of the bone with, for example, scribing, pointing or clicking operations, that is, the distal end of the trackable element 1 performs an abutting operation on the surface of the bone, the abutting operation including scribing, pointing or clicking operations on the surface of the bone. When the switch meets a third setting condition, the control device is triggered to obtain the position information of the distal end of the trackable element 1, and the control device obtains the surface profile data of the bone from the position information of the end of the trackable element 1. Further, the control device directly obtains the mark point information based on the surface profile data of the bone and performs virtual reconstruction of the bone surface based on the mark point information in combination with the bone image data obtained in advance. FIG. 6 illustrates the virtual reconstruction area 41 obtained from the virtual reconstruction of the bone surface. Specifically, after the bone registration system is turned on, the operator turns on the manual switch 35 and communicatively connects the trackable element 1 to the positioning device 2. CT images collected before the surgery is pre-stored in the memory of the control device. In some embodiments, the CT images collected before the surgery is obtained remotely and stored in a memory separated from the control device. The distal end of the trackable element 1 is configured to scribe or click on the bone surface. For example, the operator places the distal end of the trackable element 1 in the target area, and presses and holds the manual switch 35 (an optional case meeting the third setting condition), and moves the trackable element 1 on the surface of the bone, so that the distal end of the trackable element 1 scribes or clicks on the surface of the bone. After the scribing or clicking on the surface of the bone is completed, the operator releases hands from the manual switch 35 and removes the distal end of the trackable element 1 from the surface of the bone. The optical position finder tracks the position of the trajectory of the target balls 34 at the distal end of the trackable element 1 and further processes and obtains the position information (mark point set) of a series of mark points on the bone surface and sends it to the control device. The control device then performs a virtual reconstruction of the bone surface according to the obtained position information of a series of mark points.

Preferably, performing virtual reconstruction of the bone surface includes: registering a mark point set of the distal end of the trackable element 1 with a positioning device 2 and a surface point set resulting from segmenting the image data of the bone. As shown in FIG. 2, specifically, the origin of the target coordinate system at a certain time under the optical position finder is O={x, y, z}, and the conversion relationship between the origin of the target coordinate system and the distal end of the trackable element 1 is T={t_i, i=1, 2 . . . n}. In this way, in the coordinate system of the positioning device 2, at a certain time, a plurality of mark point sets are P={p_i, i=1, 2, . . . n}, where p_i=O·t_i, the mark point sets are precisely registered with the surface point set $Q_i$ having been segmented and reconstructed (in other word, with the surface point set under the coordinate system of the image data of the bone). As a result, the virtual reconstruction of the bone surface can be achieved.

Further, registering a mark point set of the distal end of the trackable element with a positioning device and a surface point set resulting from segmenting the image data of the bone comprises:

transferring the mark point set $P_i$ to a coordinate system in which the surface point set $Q_i$ is located:

$$Q_i = R \cdot P_i + T$$

where R and T are rotation and translation matrices, and i is a natural number;

wherein the rotation and translation matrices R and T are selected to obtain a minimum of an objective function E:

$$E = \sum_{i=1}^{n} \|Q_i - (P_i \cdot R + T)\|^2 = \min.$$

In other embodiments, it is unnecessary to remove the cartilage over the surface of the bone, and the distal end of the trackable element 1 performs the abutting operation on the cartilage surface so as to obtain the surface profile data of the cartilage surface. In this case, a thickness data of the cartilage surface is also required so as for conversion of the surface profile data of the cartilage surface to the surface profile data of the bone surface. Therefore, the mark point information can be obtained based on the surface profile data and the thickness data of the cartilage.

Generally, the image data the bone can be collected in advance before surgery, such as CT images collected before surgery, etc., which mainly include information of the bone. In practice, the thickness of the cartilage covering the surface of the bone can generally be considered as a fixed value. The correction value is determined according to the age, gender, and other factors of the patient to correct the thickness of the cartilage. However, the correction value determined in this way is not suitable for individual differences, and may negatively affect the accuracy of the registration of the bone and thus the accuracy of the operation. Therefore, in the bone registration method provided in this embodiment, the thickness data of the cartilage is obtained by: obtaining an information of a first position of the distal end of the trackable element when the switch of the trackable element meets a first setting condition and the distal end of the trackable element is at a selected point on the surface of the cartilage; obtaining an information of a second position of the distal end of the trackable element when the distal end of the trackable element performs a puncture operation at the selected point and when the switch meets a second setting condition; obtaining the thickness data of the cartilage based on a position variation between the first position and the second position. The cartilage thickness data obtained from the puncture operation can accurately match with individual differences, which is conducive to improving the accuracy of bone registration. Specifically, as shown in FIG. 10, the bone registration method without removing cartilage mainly includes the following steps: Step SB1: performing the abutting operation by the distal end of the trackable element on the surface of the cartilage to obtain surface profile data of the cartilage surface; Step SB2: performing a puncture operation by the distal end of the trackable element on the cartilage surface to obtain thickness data of the cartilage; Step SB3: data processing (performed by the control device, for example); Step SB4: virtual reconstruction of the bone surface (performed by the control device, for example).

Referring to FIG. 7, preferably, the distal end of the trackable element 1 is a pointed end, and the switch of the trackable element 1 is configured to trigger the control device to record an information of first position of the trackable element when the trackable element performs the puncture operation at the selected point on the surface of the cartilage and when a first setting condition is met, and to trigger the control device to record an information of second position of the trackable element when a second setting condition is met during the puncture operation; and the control device is configured to obtain the thickness data of the cartilage according to a position variation between the first position and the second position. Further, the trackable element 1 may send the thickness data of the cartilage to the control device, and the control device then corrects the surface profile data of the cartilage based on the thickness data of the cartilage to obtain the surface profile data of the bone for virtual reconstruction of the bone surface. The process of virtual reconstruction can refer to the said related part of the present application. More preferably, the bone surface includes a plurality of selected points, wherein the cartilage thickness data is an average value of a plurality of data obtained from the puncture operation performed by the distal end of the trackable element 1 at a plurality of selected points. In practice, the cartilage may have different thickness at different selected points. In addition, the cartilage thickness data obtained from merely one puncture operation may have some errors. Therefore, a plurality of puncture operations may be performed to obtain a plurality of thickness data of the cartilage, and then the average value is preferably taken for achieving an increased accuracy.

When the distal end of the trackable element 1 performs an abutting operation on the surface of the bone at a selected point, and when the first setting condition is met, the control device for example is triggered by the switch of the trackable element 1 which is controlled automatically or manually by an operator, to record an information of first position of the trackable element 1, based on subjective feel of the operator or a setting condition configured in the trackable element 1. Then, the distal end of the trackable element 1 performs the puncture operation at selected points. When the second setting condition is met, the control device for example is triggered by the switch of the trackable element 1 which is controlled automatically or manually by an operator, to record an information of second position of the trackable element 1, based on subjective feel of the operator or a setting condition configured in the trackable element 1. Based on the above, the thickness data of the cartilage can be obtained according to a position variation between the first position and the second position.

In an exemplary example, the first setting condition includes pressing the manual switch 35, and the second setting condition includes pressing the manual switch 35 again. The manual switch 35 is pressed to trigger the control device to record the information of first position of the trackable element 1 (the position information of a selected point on the surface of the cartilage) when the distal end of the trackable element 1 contacts the surface of the cartilage; and then the manual switch 35 is pressed again to trigger the control device to record the information of second position of the trackable element 1 (the position information of the selected point on the surface of the bone) when the distal end of the trackable element 1 contacts the surface of the bone during the puncture operation performed by the trackable element 1 under a downward force applied by the operator. The displacement of the trackable element 1 during the puncture operation is the thickness of the cartilage. The determination of when the manual switch 35 can be pressed is dependent to the subjective feel of the operator. In this case, there is no need to remove cartilage before registration of the bone, and thus the operation is convenient. Compared with the existing method performed by using a correction value determined directly according to the factors about the patient's age or gender, the result of the method according to the present application is more accurate, which is suitable for individual differences and effectively improves the accuracy of bone registration.

Please refer to FIG. 4, which is a schematic diagram of a trackable element 1 according to a second example of an embodiment of the present application. In this example, the switch of the trackable element 1 includes a force sensor 36 configured to sense a reactive force received by the distal end of the trackable element 1, and the first setting condition includes that the reactive force sensed by the force sensor 36 is greater than a first preset value. Optionally, the reactive force generated at the time the distal end of the trackable element 1 contacts the cartilage surface during the puncture operation is selected as a first preset value, and the first preset value is an initial zero mark. In practice, whether or not the cartilage is removed, once the reactive force sensed by the force sensor 36 is greater than the first preset value, it indicates that the distal end of the trackable element 1 has contacted the bone surface. The subsequent process of virtual reconstruction of the bone surface can refer to the foregoing, which is similar to the previous example and will not be repeated here.

Further, in the solution that cartilage is not removed, the distal end of the trackable element 1 continues to puncture at the selected point. When a second setting condition is met, the control device is triggered to record the information of second position of the trackable element 1. The second setting condition includes that the reactive force sensed by the force sensor 36 is greater than a second preset value, wherein the second preset value is greater than the first preset value. In practice, the reactive force generated at the time the distal end of the trackable element 1 contacts the bone surface during the puncture operation is selected as the second preset value, and the second preset value is an initial terminal mark. In other embodiments, the second setting condition is that the position information of the distal end of the trackable element remains unchanged during an increase of the reactive force sensed by the force sensor. Specifically, during the puncture operation of the trackable element 1, when the reactive force is always increasing but the position of the distal end of the trackable element 1 remains unchanged, this means that the distal end of the trackable element 1 has contacted the surface of the bone. Therefore, the case where the reactive force increases but the position information does not change can be used as the second setting condition, which indicates the distal end of the trackable element 1 has contacted the bone surface. Furthermore, after the information of first position and second position of the trackable element 1 are obtained, the position variation of the distal end of the trackable element 1 can be obtained through tacking the first position and the second position, and thus the thickness of the cartilage is obtained or known.

Furthermore, the switch of the trackable element 1 also includes a manual switch 35. The operator can operate the manual switch 35 in different ways to achieve various functions. For example, automatic selection or deletion of the selected points may be achieved by triggering the force sensor 36 through pressing the manual switch 35 once, pressing the manual switch 35 multiple times or long pressing the manual switch 35. Similarly, manual selection or deletion of the selected points may be achieved by deactivating the force sensor 36 through pressing the manual switch 35 once, pressing the manual switch 35 multiple times or long pressing the manual switch 35.

Please refer to FIG. 5, which is a schematic diagram of a trackable element 1 according to a third example of an embodiment of the present application. In this example, the end of the trackable element 1 is a pointed end, and the distal end of the trackable element 1 is configured for a puncture operation at a selected point on a bone surface to obtain thickness data of the cartilage at the selected point. The switch includes a displacement contact switch 37 including a damper having a stiffness allowing a stroke of the damper to match, indicate or correspond to a puncture resistance in a puncture operation performed by the distal end of the trackable element 1 through the cartilage. The displacement contact switch 37 is configured to trigger the control device to record the position information of the trackable element 1 when a preset stroke of the damper is reached. The control device is configured to obtain the thickness data of the cartilage based on the position information and the stiffness of the damper. Optionally, the damper includes a spring. In practice, the reactive force generated at the time the distal end of the trackable element 1 contacts the cartilage surface during the puncture operation is selected as an initial zero mark. Based on the stiffness of the cartilage recorded by calibration, a suitable spring is selected to obtain the relationship between the amount of the spring compression and the puncture depth of the cartilage, so that the thickness of the cartilage can be obtained from the position variation. Specifically, after determining the selected point, the operator presses the trackable element 1, and the end of the trackable element 1 receives the reactive force from the tissue of the cartilage. The distal end of the trackable element 1 moves axially relative to the displacement contact switch 37. When the distal end of the trackable element 1 reaches the bone, a preset stroke of the spring is reached, and the displacement contact switch 37 is activated, thereby triggering the control device to record the position information of the trackable element 1. Preferably, after the displacement contact switch 37 is installed, the configuration of the displacement switch is visible, that is, the operator can directly observe whether the displacement switch is activated or not. In practice, the information about the configuration of the displacement switch can be transmitted to the control device in various ways. For example, the operator can directly observe and input the information into the control device, or the trackable element 1 can directly transmit the data about the configuration of the displacement contact switch 37 wirelessly to the control device. The control device can then conveniently obtain the thickness data of the cartilage based on the calibrated spring stiffness. For further virtual reconstruction operations, refer to the foregoing, which is similar to other examples and will not be repeated here.

In the above embodiments, the operator can independently complete the point selection and registration through the switch provided on the trackable element 1, which improves the efficiency of preoperative preparation and the operator's use experience. In practice, it is also possible that the control signal is input by another operator through another input device. Optionally, the input device may be a keyboard, a mouse, a touch screen, and the like.

In addition, according to another aspect of the present application, the bone registration method as described above may be implemented when a program is executed, and the program may be stored in a memory of a control device of the bone registration system provided by the present application. It is possible to integrate the above program into other hardware devices, such as any device of the bone registration system.

In summary, in the method, system, control device for registration of a bone, and the trackable element provided by the present application, it is configured to obtain a mark point information which can be obtained from a certain operation performed by a distal end of a trackable element on a surface of the bone when a switch of the trackable element meets a setting condition corresponding to the operation; and to perform a virtual reconstruction of the surface of the bone according to the obtained mark point information and an image data of the bone which is obtained in advance. As a result, the control device of the trackable element can be triggered automatically or manually by the operator, to record the position information of the trackable element, such as the information of first position and/or the information of second position described above, and the data about the surface correction of the cartilage can be also obtained and transmitted to the control device, so that the control device can perform the virtual reconstruction of the bone surface. As a result, a precise registration of the patient's physical space coordinate system and image space coordinate system can be achieved, during which only one operator is enough for completing the registration. Therefore, operations with high accuracy and convenience are ensured, which can significantly improve the registration efficiency, and the operating experience of operators.

Further, the navigation system includes an optical positioning system, and the positioning target of the optical positioning system is arranged on the trackable element, which not only avoids the problems of inaccurate registration of mark points and large registration error in the case of only using bone-related mark points, but also saves the cost thanks to using the optical positioning system.

The above description is a description of the embodiments of the present application, and does not limit the scope of the present application. Any changes and modifications made by those skilled in the art in accordance with the above disclosure are within the scope of the claims.

The invention claimed is:

1. A registration method for a bone, comprising:
   obtaining a mark point information through an operation performed by a distal end of a trackable element on a surface of the bone when a switch of the trackable element meets a setting condition corresponding to the operation;
   performing a virtual reconstruction of the surface of the bone according to the obtained mark point information and an image data of the bone;
   wherein a step of performing a virtual reconstruction of the surface of the bone comprises:

registering a mark point set of the distal end of the trackable element with a positioning device and a surface point set resulting from segmenting the image data of the bone;

wherein registering a mark point set of the distal end of the trackable element with a positioning device and a surface point set resulting from segmenting the image data of the bone comprises:

transferring the mark point set $P_i$ to a coordinate system in which the surface point set $Q_i$ is located:

$$Q_i = R \cdot P_i + T$$

where R and T are rotation and translation matrices, and i is a natural number;

wherein the rotation and translation matrices R and T are selected to obtain a minimum of an objective function E:

$$E = \sum_{i=1}^{n} \|Q_i - (P_i \cdot R + T)\|^2 = \min.$$

2. The registration method according to claim 1, wherein the mark point information is obtained based on a surface profile data and a thickness data of a cartilage; or the mark point information is obtained based on a surface profile data of the bone;

wherein the surface profile data of the cartilage is obtained through an abutting operation performed by the distal end of the trackable element on a surface of the cartilage;

wherein the surface profile data of the bone is obtained through an abutting operation performed by the distal end of the trackable element on a surface of the bone;

wherein the thickness data of the cartilage is obtained by:

obtaining an information of a first position of the distal end of the trackable element when the switch of the trackable element meets a first setting condition and the distal end of the trackable element is at a selected point on the surface of the cartilage;

obtaining an information of a second position of the distal end of the trackable element when the distal end of the trackable element performs a puncture operation at the selected point and when the switch meets a second setting condition;

obtaining the thickness data of the cartilage based on a position variation between the first position and the second position.

3. The registration method according to claim 1, wherein the mark point information is obtained based on a surface profile data and a thickness data of a cartilage;

wherein the surface profile data of the cartilage is obtained through an abutting operation performed by the distal end of the trackable element on a surface of the cartilage;

wherein the switch comprises a displacement contact switch with a damper, and the damper has a stiffness configured to allow a stroke of the damper to match a puncture resistance in a puncture operation performed by the distal end of the trackable element on the cartilage;

wherein the thickness data of the cartilage is obtained by:

obtaining a position information of the distal end of the trackable element when the distal end of the trackable element performs the puncture operation at a selected point and reaches a preset stroke of the damper;

obtaining the thickness data of the cartilage based on the stiffness of the damper and the position information.

4. The registration method according to claim 2, wherein the mark point information is obtained based on the surface profile data of the cartilage and the thickness data of the cartilage;

wherein the thickness data of the cartilage comprises an average of a plurality of data obtained from puncture operations performed by the distal end of the trackable element on a plurality of selected points.

5. The registration method according to claim 3, wherein the mark point information is obtained based on the surface profile data of the cartilage and the thickness data of the cartilage;

wherein the thickness data of the cartilage comprises an average of a plurality of data obtained from puncture operations performed by the distal end of the trackable element on a plurality of selected points.

6. A registration system for a bone, comprising: a trackable element, a positioning device and a control device;

wherein the trackable element is configured to perform an operation on a surface of the bone;

wherein the positioning device is communicatively connected to the trackable element and the control device, and the positioning device is configured to obtain a position information of the trackable element and send the position information to the control device;

wherein the trackable element comprises a switch communicatively connected to the control device, and the control device is triggered to obtain the position information of the trackable element when the switch meets a setting condition corresponding to the operation; and wherein the control device is configured to obtain a mark point information based on the position information, and perform a virtual reconstruction of the surface of the bone according to the mark point information in combination with an image data of the bone;

wherein performing a virtual reconstruction of the surface of the bone comprises:

registering a mark point set of the distal end of the trackable element with a positioning device and a surface point set resulting from segmenting the image data of the bone;

wherein registering a mark point set of the distal end of the trackable element with a positioning device and a surface point set resulting from segmenting the image data of the bone comprises:

transferring the mark point set $P_i$ to a coordinate system in which the surface point set $Q_i$ is located:

$$Q_i = R \cdot P_i + T$$

where R and T are rotation and translation matrices, and i is a natural number;

wherein the rotation and translation matrices R and T are selected to obtain a minimum of an objective function E:

$$E = \sum_{i=1}^{n} \|Q_i - (P_i \cdot R + T)\|^2 = \min.$$

7. The registration system according to claim 6, wherein: a distal end of the trackable element is a pointed end; the distal end of the trackable element is configured to perform an abutting operation on a surface of a cartilage and to perform a puncture operation at a selected point on the surface of the cartilage; the control device is configured to:
obtain a surface profile data of the cartilage according to the abutting operation performed by the distal end of the trackable element against the surface of the cartilage, to obtain a thickness data of the cartilage according to the puncture operation performed by the distal end of the trackable element on the surface of the cartilage, and to obtain the mark point information based on the surface profile data and thickness data of the cartilage; or
a distal end of the trackable element is configured to perform an abutting operation on the surface of the bone; the control device is configured to obtain a surface profile data of the bone according to the abutting operation performed by the distal end of the trackable element against the surface of the bone, and to obtain the mark point information based on the surface profile data of the bone.

8. The registration system according to claim 7, wherein the switch is configured to trigger the control device to record an information of first position of the trackable element when the trackable element performs the puncture operation at the selected point on the surface of the cartilage and when a first setting condition is met, and to trigger the control device to record an information of second position of the trackable element when a second setting condition is met during the puncture operation; and the control device is configured to obtain the thickness data of the cartilage according to a position variation between the first position and the second position.

9. The registration system according to claim 8, wherein the switch comprises a manual switch or a force sensor configured to sense a force received by the distal end of the trackable element;
the first setting condition comprises:
the manual switch is pressed; or
the force sensed by the force sensor is greater than a first preset value;
the second setting condition comprises:
the manual switch is pressed again;
the force sensed by the force sensor is greater than a second preset value, wherein the second preset value is greater than the first preset value; or
the position information of the distal end of the trackable element remains unchanged during an increase of the force sensed by the force sensor.

10. The registration system according to claim 7, wherein the distal end of the trackable element is a pointed end, and the distal end of the trackable element is configured to perform a puncture operation at the selected point on the surface of the cartilage;
wherein the switch comprises a displacement contact switch comprising a damper, and the damper has a stiffness configured to allow a stroke of the damper to match a puncture resistance in a puncture operation performed by the distal end of the trackable element through the cartilage; the displacement contact switch is configured to trigger the control device to record the position information of the trackable element when a preset stroke of the damper is reached; the control device is configured to obtain the thickness data of the cartilage based on the position information and the stiffness of the damper.

11. The registration system according to claim 7, wherein the switch is configured to trigger the control device to record the position information of the distal end of the trackable element when a third setting condition is met; the control device is configured to obtain the surface profile data of the cartilage or the surface profile data of the bone according to the position information.

12. The registration system according to claim 6, further comprising a display device communicatively connected to the control device, wherein the display device is configured to display the position information of the trackable element, selected points on the surface of the bone, results of the virtual reconstruction, or a moving trajectory of the trackable element.

13. The registration system according to claim 6, wherein the positioning device comprises an optical locator, and the trackable element comprises a plurality of optical targets;
wherein the optical locator is configured to position the optical targets with infrared rays.

14. A trackable element, comprising: a switch and a plurality of targets, wherein the targets are tracked by a positioning device; and the switch is configured to trigger a control device to obtain a position information of a distal end of the trackable element when a setting condition is met;
wherein the control device is configured to obtain a mark point information based on the position information, and perform a virtual reconstruction of the surface of the bone according to the mark point information in combination with an image data of the bone;
wherein performing a virtual reconstruction of the surface of the bone comprises:
registering a mark point set of the distal end of the trackable element with a positioning device and a surface point set resulting from segmenting the image data of the bone;
wherein registering a mark point set of the distal end of the trackable element with a positioning device and a surface point set resulting from segmenting the image data of the bone comprises:
transferring the mark point set $P_i$ to a coordinate system in which the surface point set $Q_i$ is located:

$$Q_i = R \cdot P_i + T$$

where R and T are rotation and translation matrices, and i is a natural number;
wherein the rotation and translation matrices R and T are selected to obtain a minimum of an objective function E:

$$E = \sum_{i=1}^{n} \|Q_i - (P_i \cdot R + T)\|^2 = \min.$$

15. The trackable element according to claim 14, wherein the distal end of the trackable element is a pointed end, and the distal end of the trackable element is configured to perform a puncture operation at a selected point on a surface of a cartilage;
wherein the switch is configured to trigger the control device to obtain an information of first position of the trackable element when a first setting condition is met, and to trigger the control device to obtain an information of second position of the trackable element when a second setting condition is met during the puncture operation.

16. The trackable element according to claim 15, wherein the switch comprises a manual switch or a force sensor configured to sense a force received by the distal end of the trackable element;

the first setting condition comprises:

the manual switch is pressed; or the reactive force sensed by the force sensor is greater than a first preset value;

the second setting condition comprises:

the manual switch is pressed again;

the force sensed by the force sensor is greater than a second preset value, wherein the second preset value is greater than the first preset value; or the position information of the distal end of the trackable element remains unchanged during an increase of the reactive force sensed by the force sensor.

17. The trackable element according to claim 14, wherein the distal end of the trackable element is a pointed end, and the distal end of the trackable element is configured to perform a puncture operation at a selected point on a surface of a cartilage;

wherein the switch comprises a displacement contact switch comprising a damper, and the damper has a stiffness configured to allow a stroke of the damper to match a puncture resistance in a puncture operation performed by the distal end of the trackable element through the cartilage; the displacement contact switch is configured to trigger the control device to obtain the position information of the trackable element when a preset stroke of the damper is reached.

18. The trackable element according to claim 14, wherein the distal end of the trackable element is configured to perform an abutting operation on a surface of a cartilage or a surface of a bone, and the switch is configured to trigger the control device to record the position information of the distal end of the trackable element when a third setting condition is met.

\* \* \* \* \*